(12) United States Patent
Dubois et al.

(10) Patent No.: US 7,557,134 B2
(45) Date of Patent: *Jul. 7, 2009

(54) N-(HETEROARYL)-1H-INDOLE-2-CARBOXAMIDE DERIVATIVES AND THEIR USE AS VANILLOID $TRPV_1$ RECEPTOR LIGANDS

(75) Inventors: Laurent Dubois, le Plessis-Robinson (FR); Yannick Evanno, Dannemois (FR); Andre Malanda, Villejust (FR)

(73) Assignee: Sanofi-Aventis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/143,066

(22) Filed: Jun. 20, 2008

(65) Prior Publication Data
US 2008/0255131 A1    Oct. 16, 2008

Related U.S. Application Data

(63) Continuation of application No. 11/765,687, filed on Jun. 20, 2007, now Pat. No. 7,407,950, which is a continuation of application No. PCT/FR2006/000008, filed on Jan. 4, 2006.

(30) Foreign Application Priority Data

Jan. 7, 2005    (FR) .................................. 05 50068

(51) Int. Cl.
*A61K 31/404*    (2006.01)
(52) U.S. Cl. ..................................... 514/414
(58) Field of Classification Search ................... 514/414
See application file for complete search history.

(56) References Cited

U.S. PATENT DOCUMENTS

2005/0165049 A1    7/2005    Hulme et al.

FOREIGN PATENT DOCUMENTS

| WO | WO 03/068749 | 8/2003 |
|---|---|---|
| WO | WO 2004/072069 | 8/2004 |
| WO | WO 2004/965784 | 11/2004 |
| WO | WO 2004/108133 | 12/2004 |
| WO | WO 2006/024776 | 3/2006 |

OTHER PUBLICATIONS

Gunthorpe et al. Current Pharmaceutical Design 2008, 14, 32-41.*
Menendez, L., et. al., Analgesic Effects of Capsazepine and Resiniferatoxin on Bone Cancer Pain in Mice, Neuroscience Letters, vol. 393, (2006), pp. 70-73.
Nagy, I., et. al., The Role of the Vanilloid (Capsaicin) Receptor (TRPV1) in Physiology and Pathology, European Journal of Pharmacology, vol. 500, No. 1-3, pp. 351-369, (2004).
Szallasi, A., et. al., TRPV1: A Therapeutic Target For Novel Analgesic Drugs?, Trends in Molecular Medicine, vol. 12, No. 11, pp. 545-554, (2006).
Szallasi, A., et. al., The Vanilloid Receptor TRPV1: 10 Years from Channel Cloning to Antagonist Proof-of-Concept, Nature Reviews, Drug Discovery, vol. 6, pp. 357-372, (2007).

* cited by examiner

*Primary Examiner*—Rebecca L Anderson
*Assistant Examiner*—Jason Nolan
(74) *Attorney, Agent, or Firm*—Balaram Gupta

(57) ABSTRACT

The invention concerns therapeutic uses of compounds of general formula (I), wherein n, $X_1$, $X_2$, $X_3$, $X_4$, $Z_1$, $Z_2$, $Z_3$, $Z_4$, $Z_5$ and W are as defined herein.

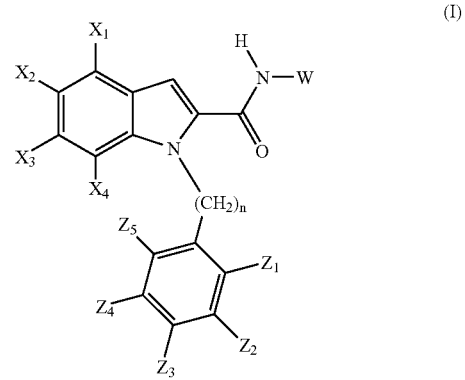

Said compounds are ligands of the $TRPV_1$ vanilloid receptor, and are therefore, useful for treating diseases associated with $TRPV_1$ receptors, such as pain and inflammation among others as disclosed and specifically claimed.

26 Claims, No Drawings

N-(HETEROARYL)-1H-INDOLE-2-CARBOXAMIDE DERIVATIVES AND THEIR USE AS VANILLOID TRPV$_1$ RECEPTOR LIGANDS

CROSS REFERENCE TO RELATED APPLICATIONS

This application is a continuation of U.S. application Ser. No. 11/765,687, filed Jun. 20, 2007, now allowed, which is a continuation of International application No. PCT/FR2006/000,008, filed Jan. 4, 2006; both of which are incorporated herein by reference in their entirety; which claims the benefit of priority of French Patent Application No. 05/50,068, filed Jan. 7, 2005.

BACKGROUND OF THE INVENTION

Field of the Invention

The invention relates to N-(heteroaryl)-1H-indole-2-carboxamide-based compounds, which show in vitro and in vivo antagonist or agonist activity for receptors of TRPV1 (or VR1) type. A first subject of the invention relates to compounds corresponding to the general formula (I) below. Another subject of the invention relates to processes for preparing the compounds of general formula (I). Another subject of the invention relates to the use of the compounds of general formula (I) especially in medicaments or in pharmaceutical compositions.

SUMMARY OF THE INVENTION

The compounds of the invention correspond to the general formula (I):

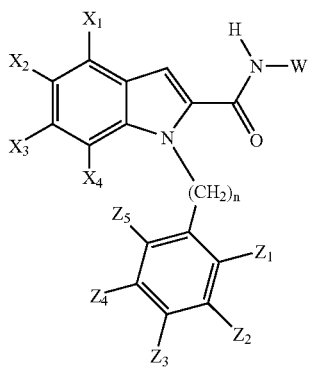

in which n is equal to 0, 1, 2 or 3;

$X_1, X_2, X_3, X_4, Z_1, Z_2, Z_3, Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)NR$_1$, R$_2$, nitro, NR$_1$, R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group; $R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

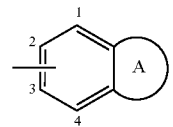

linked to the nitrogen atom via positions 1, 2, 3 or 4; A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O) —, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$- or aryl-$C_1$-$C_6$-alkylene-S(O)$_2$— or aryl group; and W is other than indolyl.

DETAILED DESCRIPTION OF THE INVENTION

In the case of the compounds of general formula (I):
the sulfur atom(s) of the heterocycle A may be in oxidized form (S(O) or S(O)$_2$);
the nitrogen atom(s) of the heterocycle A may be in oxidized form (N-oxide).

Among the compounds of general formula (I) that are subjects of the invention, a first subgroup of compounds consists of the compounds for which n is equal to 0 or 1.

Among the compounds of general formula (I) that are subjects of the invention, a second subgroup of compounds consists of the compounds for which $X_1, X_2, X_3, X_4, Z_1, Z_2, Z_3, Z_4$ and $Z_5$ represent, independently of each other, a hydrogen or halogen atom, more particularly a fluorine, or a $C_1$-$C_6$-alkyl group, more particularly a methyl, or a $C_1$-$C_6$-fluoroalkyl group, more particularly a CF$_3$, or a $C_1$-$C_6$-alkoxy group, more particularly a methoxy.

Among the compounds of general formula (I) that are subjects of the invention, a third subgroup of compounds consists of the compounds for which W is chosen from indolinyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl and tetrahydrobenzo[b][1,4]thiazepinyl groups; the carbon and/or nitrogen atom(s) of the said group W being optionally substituted as defined in the general formula (I).

Among the compounds of the third subgroup, a fourth subgroup of compounds consists of the compounds for which W is chosen from isoquinolyl, dihydroquinolyl, tetrahydroquinolyl, benzoxazinyl, dihydrobenzoxazinyl, benzofuryl, indolinyl, benzoxazolyl, indazolyl, benzimidazolyl, benzothiazolyl, benzotriazolyl, quinolyl and quinoxalinyl groups;

the carbon atom(s) of the said group W being optionally substituted with one or more groups chosen from an oxo group, $C_1$-$C_6$-alkyl, more particularly methyl or ethyl, or aryl, more particularly phenyl, as defined in the general formula (I) in relation with A; and/or the nitrogen atom(s) of the said group W being optionally substituted with $R_6$ when the nitrogen is adjacent to a carbon atom substituted with an oxo group, or with $R_7$ in the other cases, $R_6$ and $R_7$ being as defined in the general formula (I) in relation with A, with $R_6$ representing a hydrogen atom or a $C_1$-$C_6$-alkyl group, more particularly a methyl, with $R_7$ representing a hydrogen atom or a $C_1$-$C_6$-alkyl group, more particularly a methyl, or a $C_1$-$C_6$-alkyl-S(O)$_2$—, more particularly a methylsulfonyl.

A fifth subgroup of compounds consists of the compounds of general formula (I):

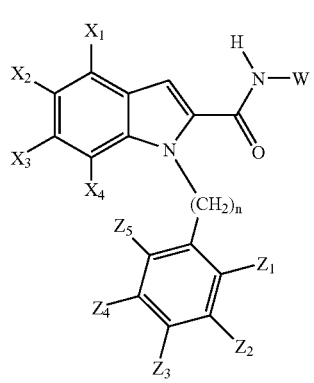

(I)

in which n is equal to 0, 1, 2 or 3;

$X_1, X_2, X_3, X_4, Z_1, Z_2, Z_3, Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

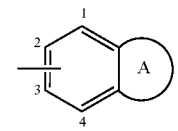

linked to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl;

on condition that when $Z_1, Z_2, Z_3, Z_4$ and $Z_5$ simultaneously represent hydrogen atoms, then n=2 or 3.

Among the compounds of general formula (I) that are subjects of the invention, a sixth subgroup of compounds consists of compounds for which W is other than quinolyl, dihydroquinolyl, tetrahydroquinolyl, isoquinolyl, dihydroisoquinolyl or tetrahydroisoquinolyl groups.

Among the compounds of general formula (I) that are subjects of the invention, a seventh subgroup of compounds consists of all of the compounds of general formula (I):

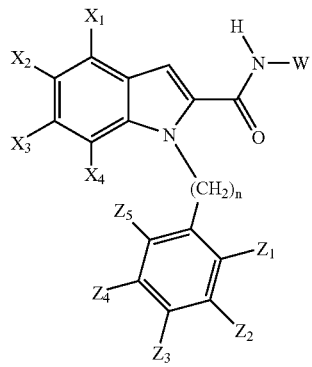

(I)

in which n is equal to 0, 1, 2 or 3;

$X_1$, $X_3$, $X_4$, $Z_1$, $Z_3$, $Z_4$ and $Z_5$ represent hydrogen atoms, $X_2$ represents a hydrogen atom, a fluorine atom or a $CF_3$ group and $Z_2$ represents a hydrogen atom or a fluorine atom;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

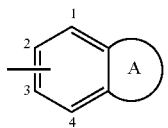

linked to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl.

Among the compounds of general formula (I) that are subjects of the invention, an eighth subgroup of compounds consists of the compounds for which W is as defined in the sixth subgroup above and $X_1$, $X_2$, $X_3$, $X_4$, $Z_1$, $Z_2$, $Z_3$, $Z_4$ and $Z_5$ are as defined in the seventh subgroup above.

Among the compounds of general formula (I) that are subjects of the invention, a ninth subgroup of compounds consists of all of the compounds of general formula (I):

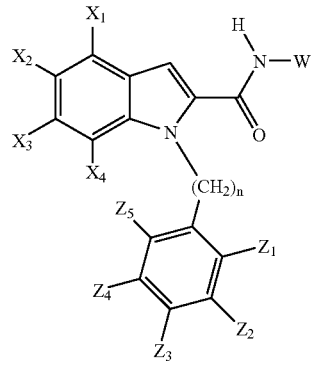

(I)

in which n is equal to 0, 1, 2 or 3;

$X_1$, $X_2$, $X_3$, $X_4$, $Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$-$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

$$\underset{3}{\overset{2}{\underset{4}{\bigcirc}}}\!\!\!-\!\!\!\overset{1}{\underset{}{\bigcirc}}\!\!\!A$$

linked to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl, the following compounds being excluded: N-(quinol-7-yl)-1-benzyl-6-bromo-1H-indole-2-carboxamide, N-(quinol-7-yl)-1-benzyl-5-bromo-1H-indole-2-carboxamide and N-(quinol-7-yl)-6-bromo-1-(4-(trifluoromethyl)benzyl)-1H-indole-2-carboxamide. These three compounds are described in document US 2005/0165049.

Among the compounds of general formula (I) that are subjects of the invention, a tenth subgroup of compounds consists of all of the compounds of general formula (I):

(I)

in which n is equal to 0, 1, 2 or 3;

$X_1$, $X_2$, $X_3$, $X_4$, $Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

$$\underset{3}{\overset{2}{\underset{4}{\bigcirc}}}\!\!\!-\!\!\!\overset{1}{\underset{}{\bigcirc}}\!\!\!A$$

linked to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo, or with $R_7$ in the other cases; $R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl;

on condition that when W is a benzimidazolyl, benzothiazolyl or benzoxazolyl group, then $Z_1$, $Z_2$, $Z_3$, $Z_4$ and $Z_5$ represent a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-fluoroalkoxy, cyano, C(O)NR$_1$R$_2$, —S(O)—$C_1$-$C_6$-alkyl, SO$_2$NR$_1$R$_2$, NR$_3$COR$_4$, NR$_3$SO$_2$R$_5$ or aryl group.

Among the compounds of general formula (I) that are subjects of the invention, an eleventh subgroup of compounds consists of all of the compounds of general formula (I):

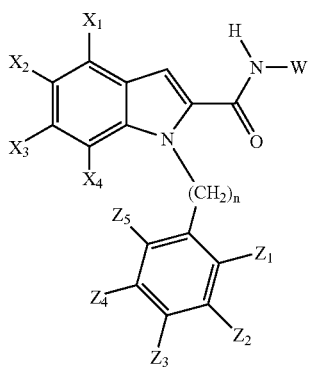

in which n is equal to 0, 1, 2 or 3;

$X_1, X_2, X_3, X_4, Z_1, Z_2, Z_3, Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$, represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

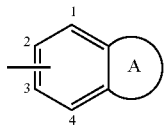

linked to the nitrogen atom via the positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl on condition that when A is a 5-membered heterocycle, then it is unsaturated.

Among the compounds of general formula (I) that are subjects of the invention, a twelfth subgroup of compounds consists of all of the compounds of general formula (I):

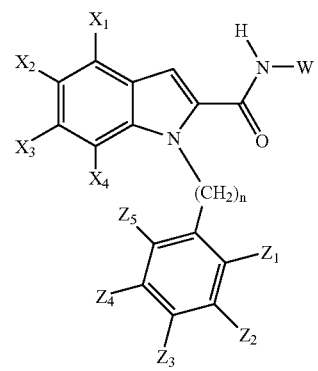

in which n is equal to 0, 1, 2 or 3;

$X_1, X_2, X_3, X_4, Z_1, Z_2, Z_3, Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)$NR_1R_2$, nitro, $NR_1R_2$, $C_1$-$C_6$-thioalkyl, —S(O)-$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

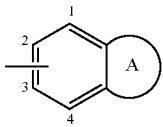

linked to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl on condition that A is other than an unsaturated 5-membered heterocycle.

The compounds for which n, $X_1$, $X_2$, $X_3$, $X_4$, $Z_1$, $Z_2$, $Z_3$, $Z_4$, $Z_5$ and W are as defined in the above subgroups of compounds form a thirteenth subgroup.

Among the compounds of general formula (I) that are subjects of the invention, a fourteenth subgroup of compounds consists of the following compounds:

N-(isoquinol-5-yl)-5-fluoro-1-[((3-trifluoromethyl)phenyl)methyl]-1H-indole-2-carboxamide,
N-(1-methyl-1,2,3,4-tetrahydroquinol-7-yl)-1-[3-(trifluoromethyl)phenyl]-1H-indole-2-carboxamide,
N-(1-methyl-1,2,3,4-tetrahydroquinol-7-yl)-1-((3-5-dimethyl)phenyl)-1H-indole-2-carboxamide,
N-(1,2,3,4-tetrahydroquinol-7-yl)-1-[3-(trifluoromethyl)phenyl]-1H-indole-2-carboxamide,
N-(4-methyl-3-oxo-2H-benzoxazin-7-yl)-1-[3-(trifluoromethyl)phenyl]-1H-indole-2-carboxamide,
N-(4-methyl-3-oxo-2H-benzoxazin-6-yl)-1-[3-(trifluoromethyl)phenyl]-1H-indole-2-carboxamide,
N-(2-oxo-3,4-dihydroquinol-7-yl)-1-[3-(trifluoromethyl)phenyl]-1H-indole-2-carboxamide,
N-(benzofuran-5-yl)-1-[3-(trifluoromethyl)phenyl]-1H-indole-2-carboxamide,
N-(1-methylindolin-5-yl)-1-[3-(trifluoromethyl)phenyl]-1H-indole-2-carboxamide,
N-(2,3-dihydrobenzoxazin-6-yl)-1-[3-(trifluoromethyl)phenyl]-1H-indole-2-carboxamide,
N-(3-oxo-2H-benzoxazin-7-yl)-1-[3-(trifluoromethyl)phenyl]-1H-indole-2-carboxamide,
N-(1-methylindolin-5-yl)-5-fluoro-1-[(3-fluorophenyl)methyl]-1H-indole-2-carboxamide,
N-(1-methyl-1,2,3,4-tetrahydroquinol-7-yl)-5-fluoro-1-[(3-fluorophenyl)methyl]-1H-indole-2-carboxamide,
N-(1,2,3,4-tetrahydroquinol-7-yl)-5-fluoro-1-[(3-fluorophenyl)methyl]-1H-indole-2-carboxamide,
N-(isoquinol-5-yl)-5-fluoro-1-[(3-fluorophenyl)methyl]-1H-indole-2-carboxamide,
N-(1,2,3,4-tetrahydroquinol-8-yl)-1-[3-(trifluoromethyl)phenyl]-1H-indole-2-carboxamide,
N-(benzoxazol-5-yl)-1-[3-(trifluoromethyl)phenyl]-1H-indole-2-carboxamide,
N-(2-methylbenzoxazol-5-yl)-1-[3-(trifluoromethyl)phenyl]-1H-indole-2-carboxamide,
N-(1-methyl-1H-indazol-5-yl)-5-trifluoromethyl-1-[(3-fluorophenyl)methyl]-1H-indole-2-carboxamide,
N-(2-oxo-3,4-dihydroquinol-7-yl)-5-fluoro-1-[(3-fluorophenyl)methyl]-1H-indole-2-carboxamide,
N-(benzofuran-5-yl)-5-fluoro-1-[(3-fluorophenyl)methyl]-1H-indole-2-carboxamide,
N-(2,3-dihydrobenzoxazin-6-yl)-5-fluoro-1-[(3-fluorophenyl)methyl]-1H-indole-2-carboxamide,
N-(3-oxo-2H-benzoxazin-6-yl)-5-fluoro-1-[(3-fluorophenyl)methyl]-1H-indole-2-carboxamide,
N-(1,2,3,4-tetrahydroquinol-7-yl)-5-trifluoromethyl-1-[(3-fluorophenyl)methyl]-1H-indole-2-carboxamide,
N-(2-oxoindolin-5-yl)-5-trifluoromethyl-1-[(3-fluorophenyl)methyl]-1H-indole-2-carboxamide,
N-(1-methylbenzimidazol-5-yl)-5-trifluoromethyl-1-[(3-fluorophenyl)methyl]-1H-indole-2-carboxamide,
N-(1-methyl-1,2,3,4-tetrahydroquinol-7-yl)-5-trifluoromethyl-1-[(3-fluorophenyl)methyl]-1H-indole-2-carboxamide,
N-(benzothiazol-6-yl)-5-trifluoromethyl-1-[(3-fluorophenyl)methyl]-1H-indole-2-carboxamide,
N-(2-methylbenzoxazol-5-yl)-5-trifluoromethyl-1-[(3-fluorophenyl)methyl]-1H-indole-2-carboxamide,
N-(2-methylbenzothiazol-5-yl)-5-trifluoromethyl-1-[(3-fluorophenyl)methyl]-1H-indole-2-carboxamide,
N-(1-methylsulfonylindolin-5-yl)-5-trifluoromethyl-1-[(3-fluorophenyl)methyl]-1H-indole-2-carboxamide,
N-(isoquinol-6-yl)-5-fluoro-1-[(3-fluorophenyl)methyl]-1H-indole-2-carboxamide,
N-(1-methylbenzimidazol-5-yl)-5-fluoro-1-[(3-fluorophenyl)methyl]-1H-indole-2-carboxamide,
N-(1-methylbenzimidazol-4-yl)-5-fluoro-1-[(3-fluorophenyl)methyl]-1H-indole-2-carboxamide,
N-(1H-benzotriazol-5-yl)-5-trifluoromethyl-1-[(3-fluorophenyl)methyl]-1H-indole-2-carboxamide,
N-(quinol-6-yl)-5-fluoro-1-[(3-fluorophenyl)methyl]-1H-indole-2-carboxamide,
N-(1-methylindazol-5-yl)-5-fluoro-1-[(3-fluorophenyl)methyl]-1H-indole-2-carboxamide,
N-(2-methylbenzoxazol-5-yl)-5-fluoro-1-[(3-fluorophenyl)methyl]-1H-indole-2-carboxamide,
N-(benzothiazol-6-yl)-5-fluoro-1-[(3-fluorophenyl)methyl]-1H-indole-2-carboxamide,
N-(2-methylbenzothiazol-5-yl)-5-fluoro-1-[(3-fluorophenyl)methyl]-1H-indole-2-carboxamide,
N-(2-oxo-3,4-dihydroquinol-7-yl)-5-trifluoromethyl-1-[(3-fluorophenyl)methyl]-1H-indole-2-carboxamide,
N-(2-oxoindolin-5-yl)-5-fluoro-1-[(3-fluorophenyl)methyl]-1H-indole-2-carboxamide,
N-(1H-benzotriazol-5-yl)-5-fluoro-1-[(3-fluorophenyl)methyl]-1H-indole-2-carboxamide,
N-(1-methylsulfonylindolin-5-yl)-5-fluoro-1-[(3-fluorophenyl)methyl]-1H-indole-2-carboxamide, N-(1,2-dimethylbenzimidazol-5-yl)-5-fluoro-1-[(3-fluorophenyl)methyl]-1H-indole-2-carboxamide,
N-(2-ethylbenzoxazol-5-yl)-5-trifluoromethyl-1-[(3-fluorophenyl)methyl]-1H-indole-2-carboxamide,
N-(2-phenylbenzoxazol-5-yl)-5-trifluoromethyl-1-[(3-fluorophenyl)methyl]-1H-indole-2-carboxamide,
N-(quinoxalin-6-yl)-5-fluoro-1-[(3-fluorophenyl)methyl]-1H-indole-2-carboxamide,
N-(quinol-7-yl)-5-fluoro-1-[(3-fluorophenyl)methyl]-1H-indole-2-carboxamide,
N-(isoquinol-7-yl)-5-fluoro-1-[(3-fluorophenyl)methyl]-1H-indole-2-carboxamide,
N-(2-methylbenzimidazol-5-yl)-5-fluoro-1-[(3-fluorophenyl)methyl]-1H-indole-2-carboxamide,
N-(benzimidazol-5-yl)-5-fluoro-1-[(3-fluorophenyl)methyl]-1H-indole-2-carboxamide,
N-(2-oxo-3,4-dihydroquinol-7-yl)-6-methoxy-1-[(4-fluorophenyl)methyl]-1H-indole-2-carboxamide and
N-(1-methylbenzimidazol-6-yl)-5-fluoro-1-[(3-fluorophenyl)methyl]-1H-indole-2-carboxamide.

In the context of the present invention, the following meanings apply:

$C_t$-$C_z$ in which t and z may take the values from 1 to 7: a carbon-based chain possibly containing from t to z carbon atoms, for example $C_1$-$C_3$ is a carbon-based chain that may contain from 1 to 3 carbon atoms;

an alkyl: a saturated, linear or branched aliphatic group. Examples that may be mentioned include methyl, ethyl, propyl, isopropyl, butyl, isobutyl, tert-butyl, pentyl, etc. groups;

an alkylene: a saturated, linear or branched divalent alkyl group, for example a $C_{1-3}$-alkylene group represents a linear or branched divalent carbon-based chain of 1 to 3 carbon atoms, more particularly a methylene, ethylene, 1-methylethylene or propylene;

a cycloalkyl: a cyclic carbon-based group. Examples that may be mentioned include cyclopropyl, cyclobutyl, cyclopentyl, cyclohexyl, etc. groups;

a fluoroalkyl: an alkyl group of which one or more hydrogen atoms have been replaced with a fluorine atom;

an alkoxy: a radical —O-alkyl in which the alkyl group is as defined above;

a fluoroalkoxy: an alkoxy group of which one or more hydrogen atoms have been replaced with a fluorine atom;

a thioalkyl: a radical —S-alkyl in which the alkyl group is as defined above;

an aryl: a cyclic aromatic group containing between 6 and 10 carbon atoms. Examples of aryl groups that may be mentioned include phenyl and naphthyl groups;

a heterocycle: a saturated, partially unsaturated or aromatic 5- to 7-membered cyclic group comprising from one to three heteroatoms chosen from O, S and N. Examples of groups W that may be mentioned include indolinyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl and tetrahydrobenzo[b][1,4]thiazepinyl groups;

a halogen atom: a fluorine, a chlorine, a bromine or an iodine;

"oxo" means "=O";

"thio" means "=S".

The compounds of formula (I) may comprise one or more asymmetric carbon atoms. They may thus exist in the form of enantiomers or diastereoisomers.

These enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

The compounds of general formula (I) may be in the form of hydrates or solvates, i.e. in the form of associations or combinations with one or more water molecules or with a solvent. Such hydrates and solvates also form part of the invention.

In the text hereinbelow, the term "leaving group" means a group that can be readily cleaved from a molecule by breaking a heterolytic bond, with loss of an electron pair. This group may thus be readily replaced with another group, for example during a substitution reaction. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, 5$^{th}$ Edition, Wiley Interscience, 2001.

In accordance with the invention, the compounds of general formula (I) may be prepared according to the process illustrated in scheme 1 below.

According to scheme 1, the compounds of general formula (IV) may be obtained by reacting a compound of general formula (II) in which $X_1$, $X_2$, $X_3$ and $X_4$ are as defined in the general formula (I) above and B represents a $C_1$-$C_6$-alkoxy or hydroxyl group, with a compound of general formula (III), in which $Z_1$, $Z_2$, $Z_3$, $Z_4$, $Z_5$ and n are as defined in the general formula (I) above and R' represents a bromine or iodine atom, a tosylate group or any other leaving group.

When n=1, 2 or 3, the compound of general formula (III) may be an alkyl halide, such as a benzyl bromide (n=1: Kolasa T., *Bioorg. Med. Chem.* 1997, 5(3) 507) or a phenethyl iodide (n=2: Abramovitch R., *Synth. Commun.*, 1995, 25(1), 1), and the reaction may be performed in the presence of a base such as sodium hydride or potassium carbonate, in a polar solvent such as dimethylformamide, dimethyl sulfoxide or acetone.

Scheme 1

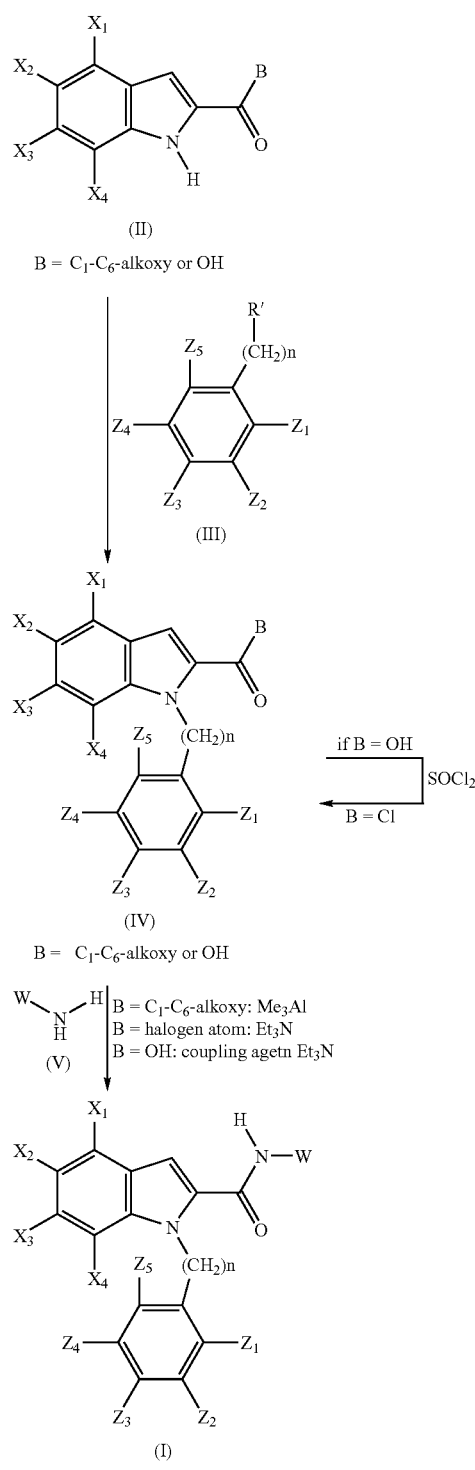

When n=0, the compound of general formula (III) is an aryl iodide or bromide and the reaction may be performed at a temperature of between 80° C. and 250° C., in the presence of a copper-based catalyst such as copper bromide or copper oxide and also a base such as potassium carbonate (Murakami Y., *Chem. Pharm. Bull.*, 1995, 43 (8), 1281). The milder conditions described in S. L. Buchwald, *J. Am. Chem. Soc.* 2002, 124, 11684 may also be used.

Alternatively, the compounds of general formula (IV), in which n=0, may be obtained by reacting the compound of general formula (II) with a compound of general formula (III) of boronic acid type (n=0, R'=B(OH)$_2$), in the presence of a base such as triethylamine or pyridine and also copper diacetate, by analogy with protocols described in W. W. K. R. Mederski, *Tetrahedron*, 1999, 55, 12757.

The compounds of general formula (II) are commercially available or prepared according to many processes described in the literature (for example D. Knittel *Synthesis* 1985, 2, 186; T. M. Williams *J. Med. Chem.* 1993, 36 (9), 1291; JP2001151771A2).

In the case of the indoles of general formula (IV), in which B represents a C$_1$-C$_6$-alkoxy group, the compound of general formula (I) is obtained by reacting a compound of general formula (IV), as obtained above, with an amide of the compound of general formula (V), in which W is as defined in the general formula (I) above, at the reflux point of a solvent such as toluene. The amide of the compound of general formula (V) is prepared by the prior action of trimethylaluminum on the amines of general formula (V).

In the case of the indoles of general formula (IV), in which B represents a hydroxyl group, the carboxylic acid function may be converted beforehand into an acid halide such as an acid chloride via the action of thionyl chloride, at the reflux point of a solvent such as dichloromethane or dichloroethane. The compound of general formula (I) is then obtained by reacting the compound of general formula (IV), in which B represents a chlorine atom, with the compound of general formula (V), in the presence of a base such as triethylamine or sodium carbonate. Alternatively, the indole of general formula (IV), in which B represents a hydroxyl group, may be coupled with the compound of general formula (V) in the presence of a coupling agent such as a dialkyl carbodiimide, benzotriazol-1-yloxytris(pyrrolidinophosphonium) hexafluorophosphate, diethyl cyanophosphonate or any other coupling agent known to those skilled in the art, in the presence of a base such as triethylamine, in a solvent such as dimethylformamide.

In scheme 1, the compounds of formula (II), (III) and (V) and the other reagents, when their preparation method is not described, are commercially available or described in the literature (for example WO 2003/049702 or WO 2003/068749).

The compounds of general formulae (II), (IV) and (I), in which $X_1$, $X_2$, $X_3$, $X_4$, $Z_1$, $Z_2$, $Z_3$, $Z_4$ and/or $Z_5$ represent a cyano group or an aryl, may be obtained via a coupling reaction, catalyzed with a metal such as palladium, performed on the corresponding compounds of general formula (II), (IV) or (I), in which $X_1$, $X_2$, $X_3$, $X_4$, $Z_1$, $Z_2$, $Z_3$, $Z_4$ and/or $Z_5$ represents a bromine atom.

The compounds of general formulae (II), (IV) and (I), in which $X_1$, $X_2$, $X_3$, $X_4$, $Z_1$, $Z_2$, $Z_3$, $Z_4$ and/or $Z_5$ represent a group $C(O)NR_1R_2$, may be obtained from the corresponding compounds of general formula (II), (IV) or (I), in which $X_1$, $X_2$, $X_3$, $X_4$, $Z_1$, $Z_2$, $Z_3$, $Z_4$ and/or $Z_5$ represents a cyano group, according to methods that are described in the literature or that are known to those skilled in the art.

The compounds of general formulae (II), (IV) and (I), in which $X_1$, $X_2$, $X_3$, $X_4$, $Z_1$, $Z_2$, $Z_3$, $Z_4$ and/or $Z_5$ represent a group —S(O)-alkyl or —S(O)$_2$-alkyl, may be obtained by oxidation of the corresponding compounds of general formula (II), (IV) or (I), in which $X_1$, $X_2$, $X_3$, $X_4$, $Z_1$, $Z_2$, $Z_3$, $Z_4$ and/or $Z_5$ represents a C$_1$-C$_6$-thioalkyl group, according to methods that are described in the literature or that are known to those skilled in the art.

The compounds of general formulae (II), (IV) and (I), in which $X_1$, $X_2$, $X_3$, $X_4$, $Z_1$, $Z_2$, $Z_3$, $Z_4$ and/or $Z_5$ represent a group $NR_1R_2$, $NR_3COR_4$ or $NR_3SO_2R_5$, may be obtained from the corresponding compounds of general formula (II), (IV) or (I), in which $X_1$, $X_2$, $X_3$, $X_4$, $Z_1$, $Z_2$, $Z_3$, $Z_4$ and/or $Z_5$ represents a nitro group, for example by reduction, followed by acylation or sulfonylation, according to methods that are described in the literature or that are known to those skilled in the art.

The compounds of general formulae (II), (IV) and (I), in which $X_1$, $X_2$, $X_3$, $X_4$, $Z_1$, $Z_2$, $Z_3$, $Z_4$ and/or $Z_5$ represent a group $SO_2NR_1R_2$, may be obtained via a method analogous to that described in *Pharmazie* 1990, 45, 346, or according to methods that are described in the literature or that are known to those skilled in the art.

The compounds of general formula (I) in which $R_7$ represents a hydrogen atom may be obtained from compounds of general formula (I) in which $R_7$ represents a phenylmethyl group, by hydrogenation, for example catalyzed with palladium, or by any method described in the literature or known to those skilled in the art.

The examples that follow describe the preparation of certain compounds in accordance with the invention. These examples are not limiting and serve merely to illustrate the present invention. The numbers of the compounds given as examples refer to those given in Table 1. The elemental microanalyses, the LC-MS (liquid chromatography coupled to mass spectrometry) analyses and the IR and NMR spectra confirm the structures of the compounds obtained.

EXAMPLE 1

Compound 12

N-(1-methyl-1H-indolin-5-yl)-5-fluoro-1-[(3-fluorophenyl)methyl]-1H-indole-2-carboxamide 1.1. Ethyl 5-fluoro-1-[(3-fluorophenyl)methyl]-1H-indole-2-carboxylate A suspension of 0.207 g (1 mmol) of ethyl 5-fluoro-1H-indole-2-carboxylate, 0.173 g (1.2 mmol) of 3-fluorobenzyl chloride and 0.276 g (2 mmol) of potassium carbonate in 10 ml of dimethylformamide is stirred for 24 hours at 60° C. The reaction mixture is then cooled and poured into a mixture of ice-water and ethyl acetate. After allowing the phases to separate by settling, the organic phase is separated out and then washed with twice 50 ml of water and then with 50 ml of saturated sodium chloride solution. The solution is dried over magnesium sulfate and filtered, and the filtrate is then concentrated under reduced pressure. 0.195 g of an oil is obtained, which is used without further purification in the following step.

1.2 N-(1-methyl-1H-indolin-5-yl)-5-fluoro-1-[(3-fluorophenyl)methyl]-1H-indole-2-carboxamide (compound 12)

0.089 g (0.6 mmol) of 5-amino-1-methyl-1H-indoline (WO 2003/049702) and 0.5 ml of trimethylaluminum (2M in toluene) are added to 2 ml of toluene under argon. The mixture is heated for 2 hours at 50° C. and 0.157 g (0.5 mmol) of ethyl 5-fluoro-1-[(3-fluorophenyl)methyl]-1H-indole-2-carboxylate, obtained in step 1.1, is added. The reaction medium is refluxed for 10 minutes and left at room temperature overnight. It is poured onto ice and 1 ml of 1N hydrochloric acid is added. The resulting mixture is extracted with ethyl acetate and the organic phase is dried with magnesium sulfate and concentrated under reduced pressure. The residue is purified by preparative chromatography. 0.066 g of solid is obtained.

Melting point: 145-147° C.
$^1$H NMR (DMSO $D_6$), δ (ppm): 2.65 (s, 3H); 2.85 (t, 2H); 3.2 (t, 2H); 5.85 (s, 2H); 6.45 (d, 1H); 6.9 (m, 2H); 7.1 (m, 2H); 7.3 (m, 3H); 7.5 (m, 3H);

EXAMPLE 2

Compound 13

N-(1-methyl-1,2,3,4-tetrahydroquinol-7-yl)-5-fluoro-1-[(3-fluorophenyl)methyl]-1H-indole-2-carboxamide The process is performed according to the method described in step 1.2 of Example 1, starting with 0.185 g of 7-amino-1-methyl-1,2,3,4-tetrahydroquinol (WO 2003/049702), 0.95 ml of trimethylaluminum (2M in toluene) and 0.3 g of ethyl 5-fluoro-1-[(3-fluorophenyl)methyl]-1H-indole-2-carboxylate, obtained in step 1.1 of Example 1. 0.122 g of product is obtained.

Melting point: 159-160° C.
$^1$H NMR (DMSO $D_6$): δ (ppm): 1.85 (m, 2H); 2.65 (t, 2H); 2.8 (s, 3H); 3.15 (t, 2H); 5.85 (s, 2H); 7 (m, 7H); 7.3 (m, 2H); 7.5 (m, 2H); 10.1 (s, 1H)

EXAMPLE 3

Compound 14

N-(1,2,3,4-tetrahydroquinol-7-yl)-5-fluoro-1-[(3-fluorophenyl)methyl]-1H-indole-2-carboxamide The process is performed according to the method described in step 1.2 of Example 1, starting with 0.169 g of 7-amino-1,2,3,4-tetrahydroquinol (WO 2003/049702), 0.95 ml of trimethylaluminum (2M in toluene) and 0.3 g of ethyl 5-fluoro-1-[(3-fluorophenyl)methyl]-1H-indole-2-carboxylate, obtained in step 1.1 of Example 1. 0.033 g of product is obtained.

Melting point: 149-151° C.
$^1$H NMR (DMSO $D_6$): δ (ppm): 1.75 (m, 2H); 2.6 (t, 2H); 3.1 (t, 2H); 5.85 (s, 2H); 6.95 (m, 7H); 7.3 (m, 2H); 7.5 (m, 2H); 10.1 (s, 1H)

EXAMPLE 4

Compound 18

N-(2-methyl-benzoxazol-5-yl)-1-[3-(trifluoromethyl)phenyl]-1H-indole-2-carboxamide 0.091 ml (0.6 mmol) of diethylcyanophosphonate, 0.168 ml (0.6 mmol) of triethylamine and 0.111 g (0.6 mmol) of 5-amino-2-methylbenzoxazole hydrochloride are added to a solution of 0.152 g (0.5 mmol) of 1-[3-(trifluoromethyl)phenyl]-1H-indole-2-carboxylic acid (JP2001151771A2) in 3 ml of dimethylformamide. The mixture is stirred overnight at room temperature and concentrated under reduced pressure, and the residue is taken up in water and dichloromethane. After separation of the phases by settling, the organic phase is dried and evaporated under reduced pressure. The residue is purified by preparative chromatography. 0.102 g of solid is obtained.

Melting point: 223-225° C.
$^1$H NMR (DMSO $D_6$): δ (ppm): 2.55 (s, 3H); 7.2 (m, 3H); 7.6 (m, 3H); 7.75 (m, 5H); 7.95 (s, 1H); 10.5 (s, 1H)

EXAMPLE 5

Compound 19

N-(1-methyl-1H-indazol-5-yl)-5-trifluoromethyl-1-[(3-fluorophenyl)methyl]-1H-indole-2-carboxamide 5.1 Ethyl 5-trifluoromethyl-1-[(3-fluorophenyl)methyl]-1H-indole-2-carboxylate A solution of 2.88 g (11.2 mmol) of ethyl 5-trifluoromethyl-1H-indole-2-carboxylate (obtained by Fisher indole synthesis from 4-(trifluoromethyl)phenylhydrazine) in 50 ml of dimethylformamide is added dropwise to a suspension of 0.58 g (14.56 mmol) of sodium hydride in 5 ml of dimethylformamide cooled in an ice bath. The mixture is stirred for 2 hours at room temperature and a solution of 2.54 g (13.44 mmol) of 3-fluorobenzyl bromide in 20 ml of dimethylformamide is then added. Stirring is continued for 24 hours. 2.44 mmol of 3-fluorobenzyl bromide are added and the mixture is stirred for a further 4 hours. The solvent is evaporated off under reduced pressure and the residue is taken up in water and ethyl acetate. After separation of the phases by settling, the organic phase is separated out and then washed with twice 50 ml of water and then with 50 ml of saturated sodium chloride solution. The solution is dried over magnesium sulfate and filtered, and then the filtrate is concentrated under reduced pressure. The residue is purified by chromatography on silica gel. 2.74 g of product are obtained.

5.2. N-(1-methyl-1H-indazol-5-yl)-5-trifluoromethyl-1-[(3-fluorophenyl)methyl]-1H-indole-2-carboxamide A solution of 0.34 g (2.3 mmol) of 5-amino-1-methyl-1H-indazole (I. T. Forbes, *J. Med. Chem.* 1993, 36 (8), 1104) in 10 ml of toluene is added, on an ice bath, to a solution of 1.92 ml (3.83 mmol) of trimethylaluminum. (2M in toluene) in 5 ml of toluene. The reaction medium is maintained at 50° C. for 30 minutes. 1.92 mmol of ethyl 5-trifluoromethyl-1-[(3-fluorophenyl)methyl]-1H-indole-2-carboxylate, obtained in step 5.1, dissolved in 10 ml of toluene, is then added. The mixture is refluxed for 3 hours and allowed to cool to room temperature. 20 ml of water and 30 ml of ethyl acetate are added. The aqueous phase is extracted with ethyl acetate; the organic phases are combined and washed with water and then with saturated sodium chloride solution. The solution is dried over magnesium sulfate and filtered, and the filtrate is then concentrated under reduced pressure. The residue is purified by chromatography on a column of silica, eluting with a mixture of ethyl acetate and dichloromethane. The residue is taken up in petroleum ether, filtered, rinsed and dried under reduced pressure. 0.71 g of solid is obtained.

Melting point: 198-199° C.

$^1$H NMR (CDCl$_3$): δ (ppm): 4 (s, 3H); 5.9 (s, 2H); 6.9 (m, 2H); 7 (m, 1H); 7.3 (m, 1H); 7.6 (m, 4H); 7.8 (d, 1H); 8 (s, 1H); 8.2 (d, 2H); 10.6 (s, 1H).

EXAMPLE 6

Compound 20

N-(1H-2-oxo-3,4-dihydroquinol-7-yl)-5-fluoro-1-[(3-fluorophenyl)methyl]-1H-indole-2-carboxamide 0.097 g (0.6 mmol) of 7-amino-1H-3,4-dihydroquinol-2-one (WO 2003/049702) and 0.5 ml of trimethylaluminum (2M in toluene) are added to 2 ml of toluene under argon. The mixture is heated for 2 hours at 50° C. and 0.157 g (0.5 mmol) of ethyl 5-fluoro-1-[(3-fluorophenyl)methyl]-1H-indole-2-carboxylate, obtained in step 1.1 of Example 1, dissolved in 1 ml of toluene, is added. The reaction medium is refluxed for 2 hours and left at room temperature overnight. It is poured onto ice and 2 ml of 1N hydrochloric acid are added. The resulting mixture is extracted with ethyl acetate and the organic phase is dried with magnesium sulfate and concentrated under reduced pressure. The residue is purified by preparative chromatography. 0.047 g of solid is obtained.

Melting point: 277-279° C.

$^1$H NMR (DMSO D$_6$): δ (ppm): 2.4 (t, 2H); 2.8 (t, 2H); 5.85 (s, 2H); 6.9 (m, 2H); 7.1 (m, 5H); 7.4 (m, 2H); 7.5 (m, 2H); 10.05 (s, 1H); 10.4 (s, 1H)

EXAMPLE 7

Compound 22

N-(2,3-dihydrobenzoxazin-6-yl)-5-fluoro-1-[(3-fluorophenyl)methyl]-1H-indole-2-carboxamide The process is performed according to the method described in Example 6, starting with 0.090 g of 6-amino-2,3-dihydrobenzoxazine (WO 2003/049702), 0.5 ml of trimethylaluminum (2M in toluene) and 0.157 g of ethyl 5-fluoro-1-[(3-fluorophenyl)methyl]-1H-indole-2-carboxylate, obtained in step 1.1 of Example 1. 0.061 g of product is obtained.

Melting point: 216-217° C.

$^1$H NMR (DMSO D$_6$): δ (ppm): 3.25 (t, 2H); 4.1 (t, 2H); 5.85 (s, 2H+1H); 6.55 (d, 1H); 6.9 (m, 3H); 7.1 (m, 3H); 7.3 (m, 2H); 7.5 (m, 2H); 10.1 (s, 1H)

EXAMPLE 8

Compound 23

N-(3-oxo-2H-benzoxazin-6-yl)-5-fluoro-1-[(3-fluorophenyl)methyl]-1H-indole-2-carboxamide The process is performed according to the method described in Example 6, starting with 0.107 g of 6-amino-3-oxo-2H-benzoxazine (WO 2003/049702), 0.5 ml of trimethylaluminum (2M in toluene) and 0.157 g of ethyl 5-fluoro-1-[(3-fluorophenyl)methyl]-1H-indole-2-carboxylate, obtained in step 1.1 of Example 1. 0.053 g of product is obtained.

LC-MS: M+H=434

$^1$H NMR (DMSO D$_6$): δ (ppm): 4.5 (s, 2H); 5.85 (s, 2H); 6.9 (m, 3H); 7.1 (m, 4H); 7.4 (s, 1H); 7.5 (m, 3H); 10.4 (s, 1H); 10.7 (s, 1H)

EXAMPLE 9

Compound 24

N-(1,2,3,4-tetrahydroquinol-7-yl)-5-trifluoromethyl-1-[(3-fluorophenyl)methyl]-1H-indole-2-carboxamide A solution of 0.24 g (1.64 mmol) of 7-amino-1,2,3,4-tetrahydroquinol (WO 2003/049702) in 5 ml of toluene is added, at 0° C. on an ice bath, to a solution of 1.37 ml (2.74 mmol) of trimethylaluminum (2M in toluene) in 5 ml of toluene. The reaction medium is maintained at 50° C. for 2 hours. 0.5 g (1.37 mmol) of ethyl 5-trifluoromethyl-1-[(3-fluorophenyl)methyl]-1H-indole-2-carboxylate, obtained in step 5.1 of Example 5, dissolved in 10 ml of toluene, is then added. The mixture is refluxed for 3 hours and allowed to cool to room temperature. 20 ml of ice-water, 20 ml of ethyl acetate and 20 ml of 1N hydrochloric acid are added. After filtering the mixture and separation of the phases by settling, the organic phase is washed with an alkaline solution and then with saturated sodium chloride solution. The organic phase is dried over magnesium sulfate and filtered, and the filtrate is then concentrated under reduced pressure. The residue is taken up in petroleum ether, collected by filtration and dried under reduced pressure. The product is purified by chromatography on a column of silica, eluting with a mixture of heptane and dichloromethane. The residue is recrystallized from ethanol. 0.29 g of solid is obtained.

Melting point: 203-204° C.

$^1$H NMR (DMSO): δ (ppm): 1.7 (m, 2H); 2.6 (m, 2H); 3.1 (m, 2H); 5.7 (t, 1H); 5.9 (s, 2H); 6.7 (m, 2H); 6.95 (m, 4H); 7.3 (m, 1H); 7.45 (s, 1H); 7.5 (d, 1H); 7.75 (d, 1H); 8.1 (s, 1H); 10.2 (s, 1H).

EXAMPLE 10

Compound 26

N-(1-methyl-benzimidazol-5-yl)-5-trifluoromethyl-1-[(3-fluorophenyl)methyl]-1H-indole-2-carboxamide 10.1  5-trifluoromethyl-1-[(3-fluorophenyl)methyl]-1H-indole-2-carboxylic acid A solution of 0.7 g (1.92 mol) of ethyl 5-trifluoromethyl-1-[(3-fluorophenyl)methyl]-1H-indole-2-carboxylate, obtained in step 5.1 of Example 5, and 0.21 g (3.83 mmol) of potassium hydroxide in 10 ml of methanol is heated to reflux. The mixture is concentrated under reduced pressure and the residue is taken up in water and acidified with hydrochloric acid. The precipitate is collected by filtration, rinsed with water and dried under reduced pressure. 0.69 g of solid is obtained, and is used without further purification in the following step.

10.2  N-(1-methyl-benzimidazol-5-yl)-5-trifluoromethyl-1-[(3-fluorophenyl)methyl]-1H-indole-2-carboxamide A solution of 0.32 g (0.95 mmol) of 5-trifluoromethyl-1-[(3-fluorophenyl)methyl]-1H-indole-2-carboxylic acid, obtained in step 10.1, and 0.69 ml (9.49 mmol) of thionyl chloride in 25 ml of dichloromethane is refluxed for 2 hours. The mixture is concentrated under reduced pressure, the residue is taken up in 20 ml of diethyl ether, and 0.17 g (1.14 mmol) of 5-amino-1-methylbenzimidazole and a solution of 0.2 g (1.9 mmol) of sodium carbonate in 2 ml of water are added. The mixture is stirred for 24 hours at room temperature, the organic phase is evaporated under reduced pressure and the resulting phase is extracted with ethyl acetate and dichloromethane. The organic phases are washed with water and with saturated sodium chloride solution, dried over sodium sulfate and concentrated under reduced pressure. The residue is taken up in petroleum ether, collected by filtration, washed and dried under reduced pressure. It is then purified by chromatography on a column of silica gel, eluting with a mixture of dichloromethane and ethyl acetate. The residue is taken up in petroleum ether, collected by filtration, washed and dried under reduced pressure. 0.3 g of solid is obtained.

Melting point: 223-224° C.

$^1$H NMR (DMSO), δ (ppm): 5.9 (s, 2H); 7 (m, 3H); 7.3 (m, 1H); 7.55 (m, 4H); 7.8 (d, 1H); 8.05 (s, 1H); 8.1 (d, 2H); 10.5 (s, 1H).

EXAMPLE 11

Compound 49

N-(quinol-7-yl)-5-fluoro-1-[(3-fluorophenyl)methyl]-1H-indole-2-carboxamide 11.1  5-fluoro-1-[(3-fluorophenyl)methyl]-1H-indole-2-carboxylic acid A solution of 8.3 g (26.3 mmol) of ethyl 5-fluoro-1-[(3-fluorophenyl)methyl]-1H-indole-2-carboxylate, obtained in step 1.1 of Example 1, and 5.2 g (79 mmol) of potassium hydroxide in a solution of 140 ml of ethanol and 14 ml of water is refluxed for 2 hours. The mixture is concentrated under reduced pressure and the residue is taken up in water and acidified with hydrochloric acid. The precipitate is collected by filtration, rinsed with water and dried under reduced pressure. 7.4 g of solid are obtained, and are used without further purification in the following step.

Melting point: 205-206° C.

11.2  N-(quinol-7-yl)-5-fluoro-1-[(3-fluorophenyl)methyl]-1H-indole-2-carboxamide 1 g (1.9 mmol) of benzotriazol-1-yloxytris(pyrrolidine) phosphonium hexafluorophosphate is added, with stirring and under nitrogen, to a suspension of 0.5 g (1.74 mmol) of 5-fluoro-1-[(3-fluorophenyl)methyl]-1H-indole-2-carboxylic acid, obtained in step 11.1, in 10 ml of dry dimethylformamide. After 5 minutes, 0.4 g (1.83 mmol) of 7-aminoquinoline hydrochloride (WO 2003/049702) and 0.9 g (7 mmol) of diisopropylethylamine are added. After stirring for 2 hours at room temperature and for 2 hours at 60° C., the reaction medium is poured into 100 ml of water and 50 ml of ethyl acetate. After separation of the phases by settling and extraction of the aqueous phase, the organic phases are combined, washed with water and dried over sodium sulfate. The residue is purified by chromatography on a column of silica gel, eluting with a mixture of dichloromethane and acetone. The solid obtained is recrystallized from isopropyl alcohol. 0.26 g of solid is obtained.

Melting point: 222-223° C.

$^1$H NMR (DMSO), δ (ppm): 5.95 (s, 2H); 6.95 (t, 2H); 7.05 (m, 1H); 7.2 (t, 1H); 7.35 (q, 1H); 7.45 (m, 1H); 7.55 (s, 1H); 7.65 (m, 2H); 8 (s, 2H); 8.3 (d, 1H); 8.55 (s, 1H); 8.9 (m, 1H); 11 (s, 1H).

Table 1 below illustrates the chemical structures and the physical properties of a number of compounds of general formula (I) according to the invention. In this table, the "m.p." column gives the melting points of the products in degrees Celsius (° C.). When the products were isolated in the form of an amorphous solid or an oil, they are characterized in this column by their mass ([MH]$^+$). Moreover, in the "salt" column, "—" represents a compound in free base form, whereas "HCl" represents a compound in hydrochloride form, and the ratio in parentheses is the (acid:base) ratio

TABLE 1

(I)

| No. | $X_1, X_2, X_3, X_4$ | n | $Z_1, Z_2, Z_3, Z_4, Z_5$ | W | m.p. (°C) | Salt |
|---|---|---|---|---|---|---|
| 1 | H, F, H, H | 1 | H, CF$_3$, H, H, H | isoquinol-5-yl | 208-209 | — |
| 2 | H, H, H, H | 0 | H, CF$_3$, H, H, H | 1-methyl-1,2,3,4-tetrahydroquinol-7-yl | 92-95 | — |
| 3 | H, H, H, H | 0 | H, CH$_3$, H, CH$_3$, H | 1-methyl-1,2,3,4-tetrahydroquinol-7-yl | 176-178 | — |
| 4 | H, H, H, H | 0 | H, CF$_3$, H, H, H | 1,2,3,4-tetrahydroquinol-7-yl | 140-143 | — |
| 5 | H, H, H, H | 0 | H, CF$_3$, H, H, H | 4-methyl-3-oxo-2H-benzoxazin-7-yl | 198-200 | — |
| 6 | H, H, H, H | 0 | H, CF$_3$, H, H, H | 4-methyl-3-oxo-2H-benzoxazin-6-yl | 178-180 | — |
| 7 | H, H, H, H | 0 | H, CF$_3$, H, H, H | 2-oxo-3,4-dihydroquinol-7-yl | [MH]$^+$ = 450 | — |
| 8 | H, H, H, H | 0 | H, CF$_3$, H, H, H | benzofuran-5-yl | 141-143 | — |
| 9 | H, H, H, H | 0 | H, CF$_3$, H, H, H | 1-methylindolin-5-yl | [MH]$^+$ = 436 | — |
| 10 | H, H, H, H | 0 | H, CF$_3$, H, H, H | 2,3-dihydro-benzoxazin-6-yl | 90-92 | — |
| 11 | H, H, H, H | 0 | H, CF$_3$, H, H, H | 3-oxo-2H-benzoxazin-7-yl | 214-216 | — |
| 12 | H, F, H, H | 1 | H, F, H, H, H | 1-methylindolin-5-yl | 145-147 | — |
| 13 | H, F, H, H | 1 | H, F, H, H, H | 1-methyl-1,2,3,4-tetrahydroquinol-7-yl | 159-160 | — |
| 14 | H, F, H, H | 1 | H, F, H, H, H | 1,2,3,4-tetrahydroquinol-7-yl | 149-151 | — |
| 15 | H, F, H, H | 1 | H, F, H, H, H | isoquinol-5-yl | 206-207 | — |
| 16 | H, H, H, H | 0 | H, CF$_3$, H, H, H | 1,2,3,4-tetrahydroquinol-8-yl | 93-95 | — |
| 17 | H, H, H, H | 0 | H, CF$_3$, H, H, H | benzoxazol-5-yl | 222-224 | — |
| 18 | H, H, H, H | 0 | H, CF$_3$, H, H, H | 2-methylbenzoxazol-5-yl | 223-225 | — |
| 19 | H, CF$_3$, H, H | 1 | H, F, H, H, H | 1-methylindazol-5-yl | 198-199 | — |
| 20 | H, F, H, H | 1 | H, F, H, H, H | 2-oxo-3,4-dihydroquinol-7-yl | 277-279 | — |
| 21 | H, F, H, H | 1 | H, F, H, H, H | benzofuran-5-yl | [MH]$^+$ = 403 | — |
| 22 | H, F, H, H | 1 | H, F, H, H, H | 2,3-dihydro-benzoxazin-6-yl | 216-217 | — |
| 23 | H, F, H, H | 1 | H, F, H, H, H | 3-oxo-2H-benzoxazin-6-yl | [MH]$^+$ = 434 | — |
| 24 | H, CF$_3$, H, H | 1 | H, F, H, H, H | 1,2,3,4-tetrahydroquinol-7-yl | 203-204 | — |
| 25 | H, CF$_3$, H, H | 1 | H, F, H, H, H | 2-oxoindolin-5-yl | 244-246 | — |
| 26 | H, CF$_3$, H, H | 1 | H, F, H, H, H | 1-methyl-benzimidazol-5-yl | 223-224 | — |
| 27 | H, CF$_3$, H, H | 1 | H, F, H, H, H | 1-methyl-1,2,3,4-tetrahydroquinol-7-yl | 146-147 | — |
| 28 | H, CF$_3$, H, H | 1 | H, F, H, H, H | benzothiazol-6-yl | 191-192 | — |
| 29 | H, CF$_3$, H, H | 1 | H, F, H, H, H | 2-methylbenzoxazol-5-yl | 182-183 | — |
| 30 | H, CF$_3$, H, H | 1 | H, F, H, H, H | 2-methylbenzoxazol-5-yl | 191-192 | — |

TABLE 1-continued (I)

$$\text{structure with } X_1, X_2, X_3, X_4 \text{ on indole, } N-(CH_2)_n\text{-phenyl with } Z_1, Z_2, Z_3, Z_4, Z_5, \text{ and C(=O)NH-W}$$

| No. | $X_1, X_2, X_3, X_4$ | n | $Z_1, Z_2, Z_3, Z_4, Z_5$ | W | m.p. (°C.) | Salt |
|---|---|---|---|---|---|---|
| 31 | H, CF$_3$, H, H | 1 | H, F, H, H, H | 1-methylsulfonylindolin-5-yl | 214-215 | — |
| 32 | H, F, H, H | 1 | H, F, H, H, H | isoquinol-6-yl | 139-141 | — |
| 33 | H, F, H, H | 1 | H, F, H, H, H | 1-methyl-benzimidazol-5-yl | 248-251 | — |
| 34 | H, F, H, H | 1 | H, F, H, H, H | 1-methyl-benzimidazol-4-yl | 195-197 | — |
| 35 | H, CF$_3$, H, H | 1 | H, F, H, H, H | 1H-benzotriazol-5-yl | 167-174 | — |
| 36 | H, F, H, H | 1 | H, F, H, H, H | quinol-6-yl | 208-210 | — |
| 37 | H, F, H, H | 1 | H, F, H, H, H | 1-methylindazol-5-yl | 210-211 | — |
| 38 | H, F, H, H | 1 | H, F, H, H, H | 2-methylbenzoxazol-5-yl | 188-189 | — |
| 39 | H, F, H, H | 1 | H, F, H, H, H | benzothiazol-6-yl | 167-168 | — |
| 40 | H, F, H, H | 1 | H, F, H, H, H | 2-methylbenzothiazol-5-yl | 201-202 | — |
| 41 | H, CF$_3$, H, H | 1 | H, F, H, H, H | 2-oxo-3,4-dihydroquinol-7-yl | 298-299 | — |
| 42 | H, F, H, H | 1 | H, F, H, H, H | 2-oxoindolin-5-yl | 249-250 | — |
| 43 | H, F, H, H | 1 | H, F, H, H, H | 1H-benzotriazol-5-yl | 220-221 | — |
| 44 | H, F, H, H | 1 | H, F, H, H, H | 1-methyl-sulfonylindolin-5-yl | 192-193 | — |
| 45 | H, F, H, H | 1 | H, F, H, H, H | 1,2-dimethyl-benzimidazol-5-yl | 281-282 | — |
| 46 | H, CF$_3$, H, H | 1 | H, F, H, H, H | 2-ethylbenzoxazol-5-yl | 187-189 | — |
| 47 | H, CF$_3$, H, H | 1 | H, F, H, H, H | 2-phenylbenzoxazol-5-yl | 194-195 | — |
| 48 | H, F, H, H | 1 | H, F, H, H, H | quinoxalin-6-yl | 188-189 | — |
| 49 | H, F, H, H | 1 | H, F, H, H, H | quinol-7-yl | 222-223 | — |
| 50 | H, F, H, H | 1 | H, F, H, H, H | isoquinol-7-yl | 270-272 | HCl (1:1) |
| 51 | H, F, H, H | 1 | H, F, H, H, H | 2-methyl-benzimidazol-5-yl | 195-200 | HCl (1:1) |
| 52 | H, F, H, H | 1 | H, F, H, H, H | benzimidazol-5-yl | 275-280 | HCl (1:1) |
| 53 | H, H, CH$_3$O, H | 1 | H, F, H, H, H | 2-oxo-3,4-dihydroquinol-7-yl | 255-256 | — |
| 54 | H, F, H, H | 1 | H, F, H, H, H | 1-methyl-benzimidazol-6-yl | 215-216 | — |

The compounds of the invention were subjected to in vitro and in vivo pharmacological tests that demonstrated their value as substances with therapeutic activities.

Test of Inhibition of the Current Induced with Capsaicin on rat DRGs

Primary culture of rat dorsal root ganglion (DRG) cells:

The neurons of the DRG naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% fetal calf serum, 25 mM KCl, 2 mM glutamine, 100 µg/ml gentamicin and 50 ng/ml of NGF, and then deposited on glass slides coated with laminin (0.25×10$^6$ cells per slide), which are then placed in Corning 12-well dishes. The cells are incubated at 37° C. in a humidified atmosphere containing 5% CO$_2$ and 95% air. Cytosine β-D-arabinoside (1 µM) is added 48 hours after culturing, to prevent the growth of non-neuronal cells. The slides are transferred into experimental chambers for the patch-clamp studies after 7-10 days of culturing.

Electrophysiology

The measuring chambers (volume 800 µl) containing the cell preparation are placed on the platform of an inverted microscope (Olympus IMT2) equipped with Hoffman optics (Modulation Contrast, New York) and observed at a magnification of 400×. The chambers are continuously gravity-influxed (2.5 ml/min) using a solution distributor accepting 8 inlets and whose sole outlet, consisting of a polyethylene tube (aperture 500 µm), is placed less than 3 mm from the cell under study. The "whole cell" configuration of the patch-clamp technique was used. The borosilicate-glass pipettes (resistance 5-10 MOhms) are brought to the cell by means of a 3D piezoelectric micromanipulator (Burleigh, PCd000). The overall currents (membrane potential set at −60 mV) are recorded with an Axopatch 1 D amplifier (Axon Instruments, Foster city, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 300 nM capsaicin solution induces on the DRG cells (voltage set at −70 mV) an entering cationic current. In order to minimize the desensitization of the receptors, a minimum interval of 1 minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

The percentages of inhibition of the capsaicin response (300 nM) are between 20% and 100% for the most active antagonist compounds of the invention tested at a concentration of 10 nM or 1 nM (see selected examples in Table 2).

TABLE 2

| Compound No. | % inhibition in DRG patch |
| --- | --- |
| 14 | 38% (10 nM) |
| 19 | 48% (1 nM) |
| 20 | 45% (1 nM) |

The intrinsic agonist effect of the compounds may be evaluated by measuring the current induced at various compound concentrations on the rat DRG, in the presence or absence of capsazepine.

Test of Mouse Corneal Irritation

The irritant nature of capsaicin is readily assessed on the cornea since this organ is one of the organs most densely innervated with C fibres. In this context, from preliminary experiments, the application of a very small amount of capsaicin (2 µl at a concentration of 160 µM) to the surface of the cornea of an animal leads to a certain number of stereotypic behavioral traits associated with irritation, which are easy to detect. Among these, the following are noted: blinking of the eye, rubbing of the instilled eye with the ipsilateral front paw, rubbing of the face with both front paws, scratching of the ipsilateral face with the hind paw. The duration of this behavior does not exceed the 2 minutes of observation, and the animal then resumes its normal activity. This aspect is moreover also normal. The mouse is not recluse in a corner with raised hackles and does not develop any observable sign of suffering. It may be concluded that the duration of action of capsaicin at these doses is less than 2 minutes.

Summary of the Methodology:

The principle of the series of experiments is to determine whether the compounds of the invention can influence the behavioral response induced with a given amount of capsaicin. The capsaicin is initially diluted to 25 mM in DMSO and diluted, for its final use, in Tween 80 to 10% in physiological saline. It appears, from control studies, that, under these conditions, the solvent has no effect.

In practice, the test product is administered orally and, with a delay (pretreatment time: t) that depends on the pharmacokinetic data, the animal receives an ocular instillation of 2 µl of a 160 µM capsaicin solution prepared as indicated above. During a 2-minute observation following the instillation, the number of times the instilled eye is rubbed with the ipsilateral front paw is recorded.

For a given animal, the percentage of protection is calculated as follows:

$P=100-((\text{number of scratching actions observed}/\text{mean number of scratching actions for the group treated with the solvent})\times 100)$ This percentage of protection is averaged for each group of animals (n=number of animals tested with the compound of the invention).

The percentages of protection evaluated in this model for the most active compounds of the invention, used at a dose of 1 mg/kg (po), are between 20% and 100% (see selected examples in Table 3):

TABLE 3

| Compound No. | % P - (t) at 1 mg/kg (po) - (n = 8) |
| --- | --- |
| 14 | 46% - (1 h) |
| 20 | 26% - (1 h) |

The results of these tests show that the compounds may have agonist or antagonist effects on the TRPV1 receptor. The most active antagonist compounds of the invention block the effects induced by stimulation of the TRPV1 receptors.

The compounds of the invention may thus be used for the preparation of medicaments, especially for the preparation of a medicament for preventing or treating pathologies in which the TRPV1 receptors are involved.

Thus, according to another of its aspects, a subject of the invention is medicaments that comprise a compound of formula (I), or a pharmaceutically acceptable salt, or alternatively a hydrate or a solvate of the said compound.

These medicaments find therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischemia (of the spinal column and/or the brain), neurodegeneration, hemorrhagic strokes (of the spinal column and/or of the brain) and post-stroke pain.

The compounds of the invention may be used for the preparation of a medicament for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be used to prepare a medicament for preventing and/or treating gynecological disorders, for instance vulvodynia and pain associated with salpingitis or with dysmenorrhea.

These products may also be used for the preparation of a medicament for preventing and/or treating gastrointestinal disorders such as gastro esophageal reflux disorder, stomach ulcers, duodenal ulcers, functional dyspepsia, colitis, IBS, Crohn's disease, pancreatitis, oesophagitis and biliary colic.

Similarly, the products of the present invention may be useful in the prevention and/or treatment of respiratory disorders such as asthma, coughing, COPD, bronchoconstriction and inflammatory disorders. These products may also be used for preventing and/or treating psoriasis, pruritus, dermal, ocular or mucous irritation, herpes and zona.

According to another of its aspects, the present invention relates to pharmaceutical compositions comprising a compound according to the invention as active principle. These pharmaceutical compositions contain an effective dose of at least one compound according to the invention, or a pharmaceutically acceptable salt, a hydrate or solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in a unit administration form, as a mixture with standard pharmaceutical excipients, to man and animals for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A method of treating a disease selected from the group consisting of chronic inflammatory pain, neuropathic pain, migraine and acute pain, comprising administering to a patient in need of said treatment a therapeutically effective amount of a compound of formula (I) or a pharmaceutically acceptable salt thereof:

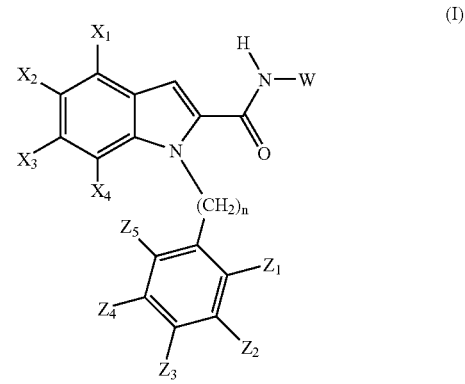

(I)

wherein
n is equal to 0, 1, 2 or 3;
$X_1$, $X_2$, $X_3$, $X_4$, $Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;

$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, said group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

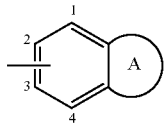

linked to the nitrogen atom via positions 1, 2, 3 or 4;
A represents a 5- to 7-membered heterocycle comprising from one to three heteroatoms chosen from O, S and N, wherein if one or more sulfur and/or nitrogen atoms are present, they are optionally in the oxidized form;
the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;
the nitrogen atom(s) of A being optionally substituted with $R_6$ when the nitrogen is adjacent to a carbon atom substituted with an oxo group, or with $R_7$ in the other cases;
$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;
$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and
W is other than indolyl or quinolyl.

2. The method according to claim 1, wherein the compound of formula (I) is having n equal to 0 or 1.

3. The method according to claim 1, wherein in the compound of formula (I): $X_1$, $X_2$, $X_3$, $X_4$, $Z_1$, $Z_2$, $Z_3$, $Z_4$ and $Z_5$ represent, independently of each other, a hydrogen or halogen atom or a $C_1$-$C_6$-alkyl, $C_1$-$C_6$-fluoroalkyl or $C_1$-$C_6$-alkoxy group.

4. The method according to claim 1, wherein in the compound of formula (I): W is chosen from indolinyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl and tetrahydrobenzo[b][1,4]thiazepinyl groups; and the carbon and/or nitrogen atom(s) of the said group W optionally being substituted as defined in the general formula (I) according to claim 1.

5. The method according to claim 1, wherein in the compound of formula (I): W is chosen from isoquinolyl, dihydroquinolyl, tetrahydroquinolyl, benzoxazinyl, dihydrobenzoxazinyl, benzofuryl, indolinyl, benzoxazolyl, indazolyl, benzimidazolyl, benzothiazolyl, benzotriazolyl, quinoxalinyl groups; the carbon atom(s) of the said group W being optionally substituted with one or more groups chosen from an oxo, $C_1$-$C_6$-alkyl or aryl group, as defined in the general formula (I) in relation with A; and/or the nitrogen atom(s) of the said group W being optionally substituted with $R_6$ when the nitrogen is adjacent to a carbon atom substituted with an oxo group, or with $R_7$ in the other cases, $R_6$ and $R_7$ being as defined in the general formula (I) according to claim 1 in relation with A, with $R_6$ representing a hydrogen atom or a $C_1$-$C_6$-alkyl group, with $R_7$ representing a hydrogen atom or a $C_1$-$C_6$-alkyl or $C_1$-$C_6$-alkyl-S(O)$_2$ group.

6. The method according to claim 1, wherein the disease is chronic inflammatory pain.

7. The method according to claim 1, wherein the disease is neuropathic pain.

8. The method according to claim 1, wherein the disease is migraine.

9. The method according to claim 1, wherein the disease is acute pain.

10. A method of treating a disease selected from the group consisting of bladder hyperactivity, bladder hyperreflexia, bladder instability, incontinence, urgent urination, urinary incontinence, cystitis, renal colic, pelvic hypersensitivity, pelvic pain, asthma and cough, comprising administering to a patient in need of said treatment a therapeutically effective amount of a compound of formula (I) or a pharmaceutically acceptable salt thereof:

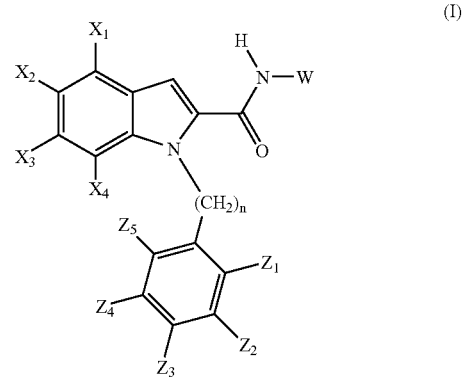

wherein
n is equal to 0, 1, 2 or 3;
$X_1$, $X_2$, $X_3$, $X_4$, $Z_1$, $Z_2$, $Z_3$, $Z_4$ and $Z_5$ represent, independently of each other, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$R$_2$, NR$_3$COR$_4$, NR$_3$SO$_2$R$_5$ or aryl group, the aryl being optionally substituted with one or more substituents chosen from a halogen and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_1$-$C_6$-fluoroalkoxy, nitro or cyano group;
$R_1$ and $R_2$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene or aryl group; or $R_1$ and $R_2$ form, together with the nitrogen atom that bears them, an azetidine, pyrrolidine, piperidine, azepine, morpholine, thiomorpholine, piperazine or homopiperazine group, said group being optionally substituted with a $C_1$-$C_6$-alkyl, $C_3$-$C_7$-cycloalkyl, $C_3$-$C_7$-cycloalkyl-$C_1$-$C_3$-alkylene or aryl group;

$R_3$ and $R_4$ represent, independently of each other, a hydrogen atom or a $C_1$-$C_6$-alkyl or aryl group;

$R_5$ represents a $C_1$-$C_6$-alkyl or aryl group;

W represents a fused bicyclic group of formula:

linked to the nitrogen atom via positions 1, 2, 3 or 4;

A represents a 5- to 7-membered heterocycle comprising from one to three heteroatoms chosen from O, S and N, wherein if one or more sulfur and/or nitrogen atoms are present, they are optionally in the oxidized form;

the carbon atom(s) of A being optionally substituted with one or more groups chosen from a hydrogen atom and a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_6$-alkylene, oxo or thio group;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene or aryl group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and W is other than indolyl or quinolyl.

11. The method according to claim 10, wherein the compound of formula (I) is having n equal to 0 or 1.

12. The method according to claim 10, wherein in the compound of formula (I): $X_1$, $X_2$, $X_3$, $X_4$, $Z_1$, $Z_2$, $Z_3$, $Z_4$ and $Z_5$ represent, independently of each other, a hydrogen or halogen atom or a $C_1$-$C_6$-alkyl, $C_1$-$C_6$-fluoroalkyl or $C_1$-$C_6$-alkoxy group.

13. The method according to claim 10, wherein in the compound of formula (I): W is chosen from indolinyl, isoindolinyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl and tetrahydrobenzo[b][1,4]thiazepinyl groups; and the carbon and/or nitrogen atom(s) of the said group W optionally being substituted as defined in the general formula (I) according to claim 10.

14. The method according to claim 10, wherein in the compound of formula (I): W is chosen from isoquinolyl, dihydroquinolyl, tetrahydroquinolyl, benzoxazinyl, dihydrobenzoxazinyl, benzofuryl, indolinyl, benzoxazolyl, indazolyl, benzimidazolyl, benzothiazolyl, benzotriazolyl, quinoxalinyl groups; the carbon atom(s) of the said group W being optionally substituted with one or more groups chosen from an oxo, $C_1$-$C_6$-alkyl or aryl group, as defined in the general formula (I) in relation with A; and/or the nitrogen atom(s) of the said group W being optionally substituted with $R_6$ when the nitrogen is adjacent to a carbon atom substituted with an oxo group, or with $R_7$ in the other cases, $R_6$ and $R_7$ being as defined in the general formula (I) according to claim 10 in relation with A, with $R_6$ representing a hydrogen atom or a $C_1$-$C_6$-alkyl group, with $R_7$ representing a hydrogen atom or a $C_1$-$C_6$-alkyl or $C_1$-$C_6$-alkyl-S(O)$_2$ group.

15. The method according to claim 10, wherein the disease is bladder hyperactivity.

16. The method according to claim 10, wherein the disease is bladder hyperreflexia.

17. The method according to claim 10, wherein the disease is bladder instability.

18. The method according to claim 10, wherein the disease is incontinence.

19. The method according to claim 10, wherein the disease is urgent urination.

20. The method according to claim 10, wherein the disease is urinary incontinence.

21. The method according to claim 10, wherein the disease is cystitis.

22. The method according to claim 10, wherein the disease is renal colic.

23. The method according to claim 10, wherein the disease is pelvic hypersensitivity.

24. The method according to claim 10, wherein the disease is pelvic pain.

25. The method according to claim 10, wherein the disease is asthma.

26. The method according to claim 10, wherein the disease is cough.

* * * * *

UNITED STATES PATENT AND TRADEMARK OFFICE
CERTIFICATE OF CORRECTION

PATENT NO.        : 7,557,134 B2
APPLICATION NO.   : 12/143066
DATED             : July 7, 2009
INVENTOR(S)       : Laurent Dubois et al.

It is certified that error appears in the above-identified patent and that said Letters Patent is hereby corrected as shown below:

In column 14, line 13, delete ""=0";" and insert -- "=O"; --, therefor.

In column 14, line 14, delete ""=S"." and insert -- "=S". --, therefor.

In column 14, line 61, delete "(Ill)"and insert -- (III) --, therefor.

In column 15, line 35, delete "alkoxy or OH" and insert -- alkoxy, OH --, therefor.

In column 16, line 2, delete " $R^1\text{==}B(OH)_2)$, " and insert -- $R' = B(OH)_2)$, --, therefor.

In column 19, line 9-27, delete "A solution of 2.88 g (11.2 mmol) of ethyl............2.74 g of product are obtained." and insert the same on Col. 19, line 10 (approx.) as a new paragraph.

In column 22, line 67, after "ratio" insert -- . --.

In column 23, in Table 1, line 57-58, delete "2-methylbenzoxazol-5-yl" and insert -- 2-methylbenzothiazol-5-yl --, therefor.

In column 25, in Table 1, line 39, delete "H, F, H, H, H" and insert -- H, H, F, H, H --, therefor.

In column 27, line 14, delete "PCd000)." and insert -- PC1000). --, therefor.

Signed and Sealed this
Third Day of July, 2012

David J. Kappos
*Director of the United States Patent and Trademark Office*